United States Patent [19]  [11] 4,076,838
Payne  [45] Feb. 28, 1978

[54] BENZOCYCLOHEPTENE-2-ACETIC ACIDS

[75] Inventor: Trevor Glyn Payne, Arlesheim, Australia

[73] Assignee: Sandoz Ltd., Basel, Switzerland

[21] Appl. No.: 737,213

[22] Filed: Nov. 1, 1976

Related U.S. Application Data

[63] Continuation-in-part of Ser. No. 625,815, Oct. 28, 1975, abandoned.

[30] Foreign Application Priority Data

Oct. 29, 1974 Switzerland ............. 14472/74

[51] Int. Cl.² ............. A61K 31/19; C07C 63/00
[52] U.S. Cl. ............. 424/317; 260/515 R
[58] Field of Search ............. 424/317; 260/515 R

[56] References Cited

U.S. PATENT DOCUMENTS

| 3,576,812 | 4/1971 | Wiesner et al. | 260/515 R |
| 3,772,378 | 11/1973 | Houlihan | 260/515 R |
| 3,904,682 | 9/1975 | Fried et al. | 260/515 R |

Primary Examiner—Stanley J. Friedman
Attorney, Agent, or Firm—Gerald D. Sharkin; Robert S. Honor

[57] ABSTRACT

This invention provides new compounds of formula I, wherein
$R_1$ is hydrogen or alkyl of 1 or 2 carbon atoms;
$R_2$ is hydrogen or halogen of atomic number from 9 to 35;

a.
 i. each of $R_3$ and $R_4$ is hydrogen, or
 ii. $R_3$ and $R_4$ together are oxygen, and
 i. $R_5$ is hydrogen or alkyl of 1 to 4 carbon atoms, or
 ii. $R_5$ and $R_7$ are attached to the same carbon atom, and form an alkylene chain of 3 to 6 carbon atoms, or
b. when A as defined hereinafter is —(CH$_2$)$_2$—
 $R_3$ is hydrogen and $R_4$ and $R_5$ together form a bond; $R_6$ is hydrogen or alkyl of 1 to 4 carbon atoms; and A is —(CH$_2$)$_n$—, wherein $n$ is 0, 1 or 2 depending on the following:
 $n$ may be 0 provided that $R_3$ and $R_4$ together are oxygen;
 $n$ may be 1 provided that (i) at least one of $R_5$, $R_6$ and $R_7$ is alkyl of 1 to 4 carbon atoms; (ii) $R_5$ and $R_7$ together form an alkylene chain of 3 to 6 carbon atoms; or (iii) $R_2$ is halogen, $R_3$ and $R_4$ are oxygen, and $R_5$, $R_6$ and $R_7$ are all hydrogen;
 $n$ may be 2 provided that (i) $R_3$ and $R_4$ together are oxygen; (ii) $R_4$ and $R_5$ together form a bond, or (iii) $R_2$ is halogen; (iv) at least one of the substituents $R_1$, $R_5$, $R_6$ and $R_7$ is alkyl of 1 to 4 carbon atoms; or (v) $R_5$ and $R_7$ together form an alkylene chain of 3 to 6 carbon atoms, or provided that $R_5$ and $R_7$ are both hydrogen, $R_6$ and A may alternatively be together with the carbon atom to which they are bound a 1,2-cycloalkylene group of formula:

wherein
 $m$ is 3 or provided that $R_3$ and $R_4$ together are oxygen alternatively 4; and
 $R_7$ is attached to any carbon atom of ring B except that marked * in the formula and is hydrogen or provided that $R_6$ is hydrogen may alternatively be alkyl of 1 to 4 carbon atoms, useful as antiphlogistics, antiarthritics and analgesics.

18 Claims, No Drawings

BENZOCYCLOHEPTENE-2-ACETIC ACIDS

This is a continuation in part of our copending application, Ser. No. 625,815 filed Oct. 28, 1975 now abandoned.

The present invention relates to new organic compounds.

In accordance with the invention there are provided new compounds of formula I,

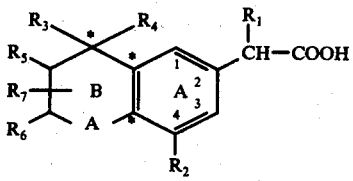

wherein
$R_1$ is hydrogen or alkyl of 1 or 2 carbon atoms;
$R_2$ is hydrogen or halogen of atomic number from 9 to 35;

a.
  i. each of $R_3$ and $R_4$ is hydrogen, or
  ii. $R_3$ and $R_4$ together are oxygen, and
  i. $R_5$ is hydrogen or alkyl of 1 to 4 carbon atoms, or
  ii. $R_5$ and $R_7$ are attached to the same carbon atom, and form an alkylene chain of 3 to 6 carbon atoms, or
b. when A as defined hereinafter is —(CH$_2$)$_2$—
$R_3$ is hydrogen and $R_4$ and $R_5$ together form a bond;
$R_6$ is hydrogen or alkyl of 1 to 4 carbon atoms; and
A is —(CH$_2$)$_n$—,
wherein $n$ is 0, 1 or 2 depending on the following:
  $n$ may be 0 provided that $R_3$ and $R_4$ together are oxygen;
  $n$ may be 1 provided that (i) at least one of $R_5$, $R_6$ and $R_7$ is alkyl of 1 to 4 carbon atoms; (ii) $R_5$ and $R_7$ together form an alkylene chain of 3 to 6 carbon atoms; or (iii) $R_2$ is halogen, $R_3$ and $R_4$ are oxygen, and $R_5$, $R_6$ and $R_7$ are all hydrogen;
  $n$ may be 2 provided that (i) $R_3$ and $R_4$ together are oxygen; (ii) $R_4$ and $R_5$ together form a bond, or (iii) $R_2$ is halogen; (iv) at least one of the substituents $R_1$, $R_5$, $R_6$ and $R_7$ is alkyl of 1 to 4 carbon atoms; or (v) $R_5$ and $R_7$ together form an alkylene chain of 3 to 6 carbon atoms; or provided that $R_5$ and $R_7$ are both hydrogen, $R_6$ and A may alternatively be together with the carbon atom to which they are bound a 1,2-cycloalkylene group of formula:

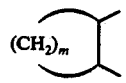

wherein
  $m$ is 3 or provided that $R_3$ and $R_4$ together are oxygen alternatively 4; and
  $R_7$ is attached to any carbon atom of ring B except that marked * in the formula and is hydrogen or provided that $R_6$ is hydrogen may alternatively be alkyl of 1 to 4 carbon atoms.

Further, in accordance with the invention, a compound of formula I may be obtained by a process comprising
a. producing a compound of formula Ia,

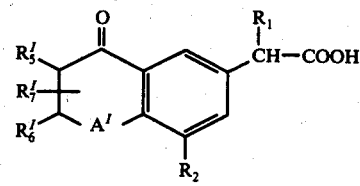

wherein
  $R_1$ and $R_2$ are as defined above,
  $R_5{}^I$ is hydrogen, alkyl of 1 to 4 carbon atoms, or, when $R_5{}^I$ and $R_7{}^I$ are bound to the same carbon atom, $R_5{}^I$ together with $R_7{}^I$ may alternatively form an alkylene chain of 3 to 6 carbon atoms,
  $R_6{}^I$ is hydrogen or alkyl of 1 to 4 carbon atoms, and
  $A^I$ is —(CH$_2$)$_{n^I}$—, wherein $n^I$ is 0, 1 or 2 with the proviso that $n$ is other than 1 when $R_2$, $R_5{}^I$, $R_6{}^I$ and $R_7{}^I$ are all hydrogen, or provided that $R_5{}^I$ and $R_7{}^I$ are both hydrogen, $R_6$ and A may alternatively be together with the carbon atom to which they are bound a 1,2-cycloalkylene group of formula:

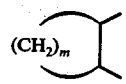

wherein $m$ is 3 or 4, and
  $R_7{}^I$ is hydrogen or provided that $R_6$ is hydrogen, may alternatively be alkyl of 1 to 4 carbon atoms,
by cyclization of a compound of formula II,

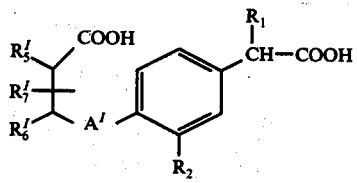

wherein
  $R_1$, $R_2$, $R_5{}^I$, $R_6{}^I$, $R_7{}^I$ and $A^I$ are as defined above,
or a reactive acid derivative thereof, or
b. producing a compound of formula Ib,

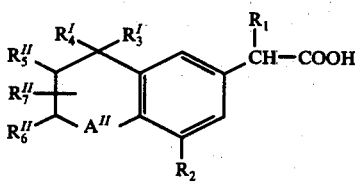

wherein
  $R_1$ and $R_2$ are as defined above, each of
  $R_3{}^I$ and $R_4{}^I$ is hydrogen,
  $R_5{}^{II}$ is hydrogen or alkyl of 1 to 4 carbon atoms, or, when $R_5{}^{II}$ and $R_7{}^{II}$ are bound to the same carbon atom, $R_5{}^{II}$ and $R_7{}^{II}$ together form an alkylene chain of 3 to 6 carbon atoms,
  $R_6{}^{II}$ is hydrogen or alkyl of 1 to 4 carbon atoms, and
  $A^{II}$ is a —(CH$_2$)$_{n^{II}}$-group,
wherein $n^{II}$ may be 1 provided that one of the substituents $R_5{}^{II}$, $R_6{}^{II}$ and $R_7{}^{II}$ is alkyl of 1 to 4 carbon atoms, or $R_5{}^{II}$ together with $R_7{}^{II}$ form an alkylene chain of 3 to 6 carbon atoms; or $n^{II}$ may be 2 provided that (i) $R_2$ is halogen; (ii) at least one of the substituents $R_1$, $R_5^{II}$, $R_6^{II}$ and $R_7^{II}$ is alkyl of 1 to 4 carbon atoms; or (iii) $R_5^{II}$ together with $R_7^{II}$ form an alkylene chain of 3 to 6 carbon atoms, or provided that $R_5^{II}$ and $R_7^{II}$ are both hydrogen, $R_6^{II}$ and $A^{II}$ together with the carbon atom to which they are bound form a 1,2-cyclopentylene group of formula

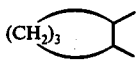

and
$R_7^{II}$ is hydrogen or when $R_6^{II}$ is hydrogen alternatively alkyl of 1 to 4 carbon atoms,
by reduction of a compound of formula III,

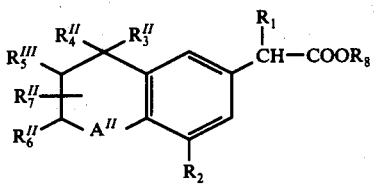

wherein
$R_1$, $R_2$, $R_6^{II}$, $R_7^{II}$ and $A^{II}$ are as defined above, (the significance of $A^{II}$ where necessary depending on $R_5^{II}$ depending instead on $R_5^{III}$),
$R_3^{II}$ and $R_4^{II}$ together are oxygen, and
$R_5^{III}$ is hydrogen or alkyl of 1 to 4 carbon atoms, or, when $R_5^{III}$ and $R_7^{II}$ are bound to the same carbon atom, $R_5^{III}$ and $R_7^{II}$ form an alkylene chain of 3 to 6 carbon atoms, or
$R_4^{II}$ and $R_5^{III}$ together form a bond and $R_3^{II}$ is hydrogen, and
$R_8$ is hydrogen, or, when $R_4^{II}$ and $R_3^{II}$ together are oxygen, a radical capable of being split off hydrolytically,
and, in case $R_8$ is a radical capable of being split off hydrolytically, concomitant removal of this radical, or c. producing a compound of formula Ic,

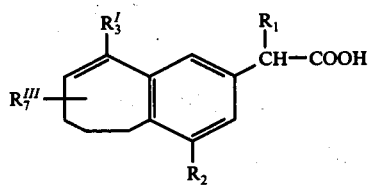

wherein
$R_1$, $R_2$ and $R_3^I$ are as defined above, and
$R_7^{III}$ is hydrogen or alkyl of 1 to 4 carbon by splitting off water, and in case $R_9$ is a radical capable of being split off acidolytically, concomitant removal of this radical from a compound of formula IV,

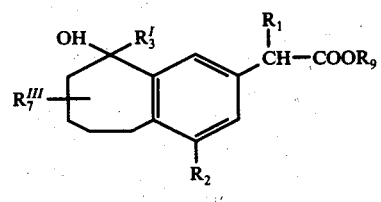

wherein
$R_1$, $R_2$, $R_3^I$ and $R_7^{III}$ are as defined above, and
$R_9$ is hydrogen or a radical capable of being removed acidolytically.

In one group of compounds $R_7$ is attached to the same carbon atom as $R_5$ and $R_6$.

In the compounds of formula I the substituent $R_1$ preferably signifies hydrogen or methyl. The substituent $R_2$ preferably signifies hydrogen. When $R_2$ is halogen as defined above, this preferably signifies chlorine. The substituents $R_3$ and $R_4$ together preferably signify oxygen or each signifies hydrogen. When the substituents $R_5$, $R_6$ or $R_7$ are lower alkyl groups, these preferably contain 1 to 3 carbon atoms and especially signify ethyl or methyl when A is a —$CH_2$-group or a —$CH_2$—$CH_2$-group, and especially signify n-propyl, isopropyl or ethyl when A is a bond. When $R_5$ and $R_7$ together form an alkylene chain, this preferably contains 5 carbon atoms. In the compounds of formula I the ring B is preferably monoalkylated. An alkyl substituent preferably is in the 6 position or, when A is a —$CH_2$-group or a —$(CH_2)_2$-group, also in the 7 position. A preferably signifies a —$(CH_2)_2$-group or together with $R_6$ and the carbon atom to which they are bound forms a cycloalkylene ring as defined above, which is preferably joined with ring B by a cis linkage.

In a further group of compounds, each of $R_2$, $R_5$ and $R_7$ signifies hydrogen, $R_1$ signifies hydrogen of alkyl of 1 or 2 carbon atoms, each of $R_2$ and $R_3$ signifies hydrogen or, together, signify oxygen, $R_6$ signifies alkyl of 1 to 4 carbon atoms and A signifies —$(CH_2)_n$-wherein $n$ is 1 or 2 or $R_6$ and A together with the carbon to which they are bonded form a 1,2-cyclopentylene ring.

The cyclization of compounds of formula II in accordance with process variant (a) may be effected in accordance with known methods. The reaction is preferably effected in the presence of a strongly acid condensation agent, optionally in the presence of an inert organic solvent, e.g. an aromatic or chlorinated hydrocarbon. Suitable acids, e.g. preferably polyphosphoric acid, sulphuric acid or methanesulphonic acid/phosphorus pentoxide. The reaction temperature may be about 60° and 160° C. In place of an acid of formula II, it is also possible to use a reactive derivative thereof for the cyclization. Suitable reactive derivatives of acids of formula II are, for example, the acid halides thereof or mixed anhydrides of acids of formula II and lower organic carboxylic acids or also lower alkyl esters of acids of formula II. In an alternative procedure, the acids of formula II may, for example, first be converted with an inorganic acid chloride, e.g. thionyl chloride, into acid chlorides thereof, and these may subsequently be cyclized under the reaction conditions of a Friedel-Crafts reaction, e.g. in the presence of aluminium trichloride, in the presence of an inert organic solvent. The reaction conditions for the hydrolysis of the organometallic complex formed as intermediates in the Friedel-Crafts reaction are preferably chosen such that any acid derivatives of the acetic acid grouping are concomitantly hydrolyzed to free acid groups.

In process variant (b), the reduction of the compounds of formula III may be effected in accordance with the usual methods for the selective reduction of a double bond or a carbonyl group to the methylene group. Suitable reduction processes are, for example, when $R_8$ is hydrogen, catalytic hydrogenation, or, in addition, when $R_3^{II}$ and $R_4^{II}$ together are oxygen, also reduction with nascent hydrogen, e.g. the reduction in accordance with Clemmensen or the reduction method in accordance with Wolff-Kishner or modifications thereof. Under the reaction conditions of Clemmensen's or Wolff-Kishner reduction, any radicals $R_8$ capable of being split off hydrolytically, e.g. alkyl, especially lower alkyl or aryl groups, are concomitantly removed from the compounds of formula III. The catalytic hydrogenation may, for example, be effected in the presence of a catalyst in an inert organic solvent at a hydrogen pressure of from 1 to 5 atmospheres. The reaction may conveniently be effected at a temperature of from 10° to 100° C. Examples of suitable catalysts are platinum or palladium catalysts or alternatively Raney nickel. Examples of suitable solvents are preferably alcohols of 1 to 6 carbon atoms or an aqueous mixture thereof or, preferably, acetic acid. The hydrogenation is preferably effected in the presence of a strong mineral acid, e.g. sulphuric or perchloric or hydrochloric acid. The reduction of compounds of formula III with nascent hydrogen may, for example, be effected in accordance with Clemmensen with amalgamated zinc/hydrochloric acid, conveniently in the presence of an inert organic solvent, e.g. an aromatic hydrocarbon or a water-miscible solvent, e.g. a lower alcohol preferably of 1 to 6 carbon atoms. The reduction is preferably effected at a temperature of from 20° to 120° C. When the Wolff-Kishner reaction is employed, the compounds of formula III may first be converted into hydrazone derivatives thereof and these are subsequently treated with strong bases, e.g. alkali metal hydroxides or alcoholates. The Wolff-Kishner reduction is preferably effected in accordance with the process variant of Huang-Minlon, for example by reacting the compounds of formula III with hydrazine hydrate in the presence of an alkali metal hydroxide and an inert, high-boiling, polar, water-miscible, organic solvent, at a temperature between about 20° and 220° C.

The removal of water from the compounds of formula IV in accordance with process variant (c) may be effected in known manner, e.g. by the action of suitable water-removing agents on the compounds of formula IV, or alternatively in the presence of an inert organic solvent. Examples of water-removing agents which may be used are strong acids or also acid anhydrides or acid halides. When $R_9$ is the compounds of formula IV is a radical capable of being split off acidolytically, e.g. an alkyl, especially lower alkyl or aryl group, the removal water of is conveniently effected with strong acids in order to achieve concomitant removal of the radical $R_9$.

The resulting compounds of formula I may be isolated and purified using conventional techniques. Where required, free forms of the compounds may be converted into corresponding salt forms in conventional manner and vice versa.

An example of such a salt form in the cyclohexylammonium salt or the (1,3-dihydroxy-2-hydroxymethyl-2-propyl)ammonium salt.

The starting materials may be obtained as follows:

a'. A compound of formula II may, for example, be obtained by hydrolyzing a compound of formula V,

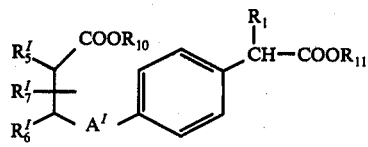

wherein $R_1$, $R_5{}^I$, $R_6{}^I$, $R_7{}^I$ and $A^I$ are as defined above, and each of $R_{10}$ and $R_{11}$ is lower alkyl, and, if desired, introducing a halogen atom $R_2$ in known manner in the resulting dicarboxylic acid. If desired, an acid of formula II may be converted in known manner into a derivative thereof, e.g. a halide.

b'. A compound of formula V may, for example, be obtained by rearrangement of a compound of formula VI,

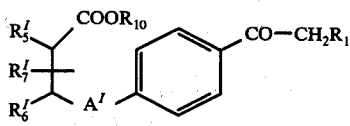

wherein $R_1$, $R_5{}^I$, $R_6{}^I$, $R_7{}^I$, $A^I$ and $R_{10}$ are as defined above, under oxidative conditions. The oxidative rearrangement may be effected in accordance with known methods, e.g. by oxidizing a compound of formula VI with thallium-III-trinitrate in the presence of a strong acid and an alcohol $R_{11}OH$.

c'. When $R_1$ is methyl or ethyl, a compound of formula VI is preferably converted in known manner into a compound of formula VII,

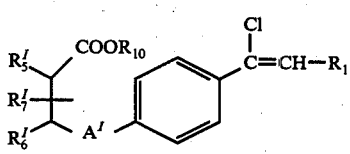

wherein $R_1$, $R_5{}^I$, $R_6{}^I$, $R_7{}^I$, $A^I$ and $R_{10}$ are as defined above, by reaction with phosphorus pentachloride in an inert aprotic solvent, removing hydrochloric acid from the compound of formula VII with sodium methylate in a dipolar aprotic solvent, e.g. dimethyl sulphoxide, and converting the resulting compound of formula VIII,

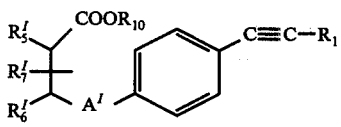

wherein $R_1$, $R_5{}^I$, $R_6{}^I$, $R_7{}^I$, $A^I$ and $R_{10}$ are as defined above, into a compound of formula V by treatment with thallium-III-trinitrate in the presence of an alcohol $R_{11}OH$.

d'. A compound of formula VI may, for example, be obtained by acylating a compound of formula IX,

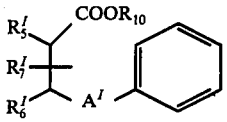

wherein $R_5^I$, $R_6^I$, $R_7^I$, $A^I$ and $R_{10}$ are as defined above, with a compound of formula X, $$R_1-CH_2-CO-Cl \qquad X$$

wherein $R_1$ is as defined above,
under the conditions of a Friedel-Crafts reaction.

e'. A compound of formula IX may, for example, be obtained by reducing a compound of formula XI,

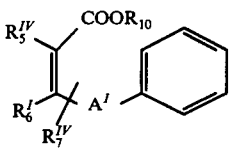

wherein
$R_6^I$, $R_{10}$ and $A^I$ are as defined above,
$R_5^{IV}$ is hydrogen or alkyl of 1 to 4 carbon atoms, and
$R_7^{IV}$ is hydrogen, or, when $R_5^{IV}$ and $R_6^I$ are hydrogen, also alkyl, by catalytic hydrogenation, and, if desired, alkylating the resulting compound of formula IXa,

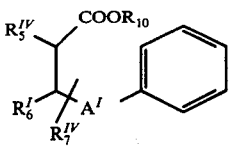

wherein $R_5^{IV}$, $R_6^I$, $R_7^{IV}$, $A^I$ and $R_{10}$ are as defined above, to a compound of formula IX disubstituted in an α position to the ester group. For alkylation in the α position to the ester group, the compound of formula IXa may be reacted in known manner with an alkali halide, or, when $R_5^{IV}$ is hydrogen, if desired also for the introduction of an $R_5^{IV}$-$R_7^{IV}$ alkylene chain with an ω-alkyl dihalide in the presence of a strongly basic condensation agent, e.g. an alkali metal amide of hydride.

f'. A compound of formula XI may, for example, be obtained by reacting a compound of formula XII,

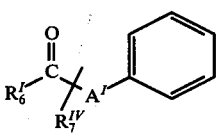

wherein $R_6^I$, $R_7^{IV}$ and $A^I$ are as defined above,
with a compound of formula XIII,

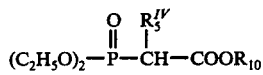

wherein $R_5^{IV}$ and $R_{10}$ are as defined above.
The reaction leads to isomeric mixtures of compounds of formula XI and the corresponding isomeric compounds wherein the ester group is in a β position to the double bond, and which are converted by catalytic hydrogen into compounds of formula IXa.

g'. A compound of formula III wherein $R_8$ is a radical capable of being split off hydrolytically, may be obtained from the corresponding acid.

h'. A compound of formula III wherein $R_4^{II}$ and $R_5^{III}$ together form a bond may, for example, be obtained by reducing the keto group to the hydroxy group in a corresponding compound of formula III wherein $R_3^{II}$ and $R_4^{II}$ together are oxygen, and subsequently removing water from the resulting hydroxy compound.

i'. A compound of formula IV may be obtained from a corresponding compound of formula Ia by reducing the keto group to the hydroxy group in this compound, if desired after the introduction of a radical $R_9$ capable of being split off acidolytically.

Insofar as the production of the starting materials is not described, these are either known or may be produced in accordance with known processes, or in a manner analogous to the processes described herein or to known processes.

Certain compounds of formula I may exist in optically active forms, e.g. those wherein at least one of $R_5$ and $R_6$ is alkyl. Such optically active forms may be prepared in conventional manner, e.g. by using optically active starting materials in the reactions mentioned above and in the Examples herein after.

In the following non-limitative Examples all temperatures are in degrees centigrade.

EXAMPLE 1:

6,7,8,9-tetrahydro-7-methyl-9-oxo-5H-benzocycloheptene-2-acetic acid 17.8 g of 5-(4-carboxymethylphenyl)-3-methylvaleric acid are added at 100°, while stirring, to 200 g of polyphosphoric acid. The reaction mixture is stirred at 100° for a further hour, is cooled to about 60°, and 100 cc of water are added dropwise thereto. The reaction mixture is then poured on ice, extracted with methylene chloride, the methylene chloride extract is washed with water and dried over sodium sulphate. The 6,7,8,9-tetrahydro-7-methyl-9-oxo-5H-benzocycloheptene-2-acetic acid, obtained after concentrating the solvent, is purified by chromatography on silica gel. The title compound has a M.P. of 105°-107° (from acetonitrile). The cyclohexylammonium salt form of the title compound has a M.P. of 135°-137° (from acetonitrile).

The starting material may be obtained as follows:

a. A solution of 292 g of (diethylphosphono)-acetic acid methyl ester in 200 cc of methanol is added dropwise at 0°-5°, while stirring, to a solution of sodium methylate (produced from 67 g of sodium) in 1000 cc of methanol. Stirring is effected at 0°-5° for a further 15 minutes, a solution of 215 g of benzyl acetone in 200 cc of methanol is added dropwise, and the mixture is stirred at room temperature for 18 hours. 55 cc of acetic acid are then added dropwise, the solution is concentrated, diluted with water and extracted with ether. The ether extract is washed with a 3% sodium bicarbonate solution, is dried over sodium sulphate and concentrated. The resulting 3-methyl-5-phenylpent-2-enoic acid methyl ester is purified by distillation. B.P. 132°-135° at 11 mm of Hg.

The 3-methyl-5-phenylpent-2-enoic acid methyl ester obtained above is dissolved in 1.5 liters of ethanol and hydrogenated at 1 atmosphere of hydrogen pressure and 25° with the addition of 10 g of palladium/charcoal (10%). After the take up of the calculated amount of hydrogen, filtration is effected and the solution is concentrated. The resulting 5-phenyl-3-methylvaleric acid methyl ester is purified by distillation. B.P. 98°–101° at 0.03 mm of Hg.

b. A solution of 20.6 g of 5-phenyl-3-methylvaleric acid methyl ester and 14.7 g of acetyl chloride in 50 cc of methylene chloride is added dropwise within 10 minutes at 0°–5°, while stirring, to a suspension of 46.5 g of aluminium chloride in 250 cc of methylene chloride. The solution is stirred at room temperature for a further 3 hours and is then poured in ice/water. The mixture is extracted with methylene chloride, the extract is washed with water, dried over sodium sulphate and concentrated. The resulting crude 5-(4-acetylphenyl)-3-methylvaleric acid methyl ester is used as such for the next reaction.

c. A solution of 17.2 g of 5-(4-acetylphenyl)-3-methylvaleric acid methyl ester in 100 cc of methanol is added with stirring to a solution of 32.2 g of thallic trinitrate and 10 cc of 70% aqueous perchloric acid in 200 cc of methanol. The reaction mixture is stirred at room temperature for 16 hours, is filtered, the filtrate is subsequently diluted with water and extracted with chloroform. After concentrating the chloroform phase which has been washed with water and dried over sodium sulphate, crude 5-(4-carbomethoxymethylphenyl)-3-methylvaleric acid methyl ester is obtained and is purified by distillation. B.P. 174°–178° at 0.05 mm of Hg.

d. A solution of 20 g of potassium hydroxide in 40 cc of water is added to a solution of 19.3 g of 5-(4-carbomethoxymethylphenyl)-3-methylvaleric acid methyl ester in 200 cc of methanol and the mixture is heated at reflux for 2 hours. The solution is subsequently concentrated, diluted with water, acidified with 2 N hydrochloric acid and extracted with ether. The crude 5-(4-carboxymethylphenyl)-3-methylvaleric acid obtained after concentrating the ether extract, is recrystallized from ether/hexane. M.P. 100°–102°.

EXAMPLE 2

5,6,7,8-tetrahydro-6,α-dimethyl-8-oxo-naphthalene-3-acetic acid

4-[4-(1-carboxyethyl)phenyl]-2-methylbutyric acid is cyclized with polyphosphoric acid in a manner analogous to that described in Example 1. The cyclohexylammonium salt of the title compound has a M.P. of 196°–199° (from methanol/ether).

The starting material may be obtained as follows:
 a. 2-methyl-4-(4-propionylphenyl)butyric acid methyl ester, produced in a manner analogous to Example 1(b), from 4-phenyl-2-methylbutyric acid acid methyl ester and propionyl chloride. B.P. 150°–154° at 0.05 mm of Hg.

b. 193 g of phosphorus pentachloride are added to a solution of 76.8 g of 2-methyl-4-(4-propionylphenyl)-butyric acid methyl ester in one liter of anhydrous ether, and the mixture is stirred at room temperature for 16 hours and is subsequently heated at reflux for one hour. The mixture is slowly poured on ice, is stirred for one hour and extracted with ether. The 4-[4-(1-chloro-1-propenyl)phenyl]-2-methylbutyric acid methyl ester obtained after evaporating the ether extract, is distilled in a vacuum (bulb type). B.P. 160°–170° at 0.06 mm of Hg.

c. 78 g of sodium methylate are added to a solution of 78 g of 4-[4-(1-chloro-1-propenyl)phenyl]-2-methylbutyric acid methyl ester in 500 cc of dimethyl sulphoxide, and the solution is stirred at room temperature for 2 hours and neutralized with 180 cc of 50% sulphuric acid. The mixture is diluted with water and extracted with ether. The ether extract is washed with water, dried over sodium sulphate and concentrated by evaporation. The resulting, oily 2-methyl-4-[4-(1-propinyl)phenyl]butyric acid methyl ester is used as such for the next reaction.

d. A solution of 64 g of 2-methyl-4-[4-(1-propinyl)phenyl]butyric acid methyl ester is added while cooling with ice to a solution of 124 g of thallium trinitrate trihydrate in 400 cc of methanol. The mixture is stirred at room temperature for 1 hour, is filtered, the filtrate is diluted with one liter of water and extracted with methylene chloride. The methylene chloride extract is washed with water, dried over sodium sulphate, concentrated by evaporation, and the resulting 4-[4-(1-carbomethoxyethyl)phenyl]-2-methylbutyric acid methyl ester is distilled in a bulb tube. B.P. 160°–170° at 0.1 mm of Hg.

e. 4-[4-(1-carboxyethyl)phenyl]-2-methylbutyric acid is produced in a manner analogous to Example 1(d). M.P. 107°–109° (from hexane/ether).

EXAMPLE 3

1-isobutyl-3-oxo-5-indanacetic acid 4-carboxymethyl-β-isobutyl-dihydrocinnamic acid is cyclized in a manner analogous to that described in Example 1. The cyclohexylamine salt of the title compound has a M.P. of 140°–142° (from methanol/ether).

The starting material may be obtained as follows:
 a. A solution of 16.2 g of 3'-methylbutyrophenone and 18 g of bromoacetic acid methyl ester in 100 cc of benzene is added dropwise, while stirring, within 30 minutes, to a suspension of 100 g of zinc dust and some crystalline iodine in 100 cc of benzene, at reflux temperature. The solution is heated at reflux for 2 hours, is cooled to room temperature, filtered, diluted with 2% hydrochloric acid and extracted with ether. The extract is washed with water, dried over sodium sulphate and concentrated. Crude β-hydroxy-β-isobutyl-dihydrocinnamic acid methyl ester is used as such for the next reaction.

A solution of 18.9 g of β-hydroxy-β-isobutyl-dihydrocinnamic acid methyl ester and 2.5 g of p-toluenesulphonic acid in 400 cc of benzene is heated at reflux (water separator) for 2 hours. The cooled solution is washed with a 1% sodium bicarbonate solution, dried over sodium sulphate and concentrated. The crude mixture of unsaturated β-isobutyl-dihydrocinnamic methyl esters is used as such for the next reaction.

15.8 g of the mixture of unsaturated esters obtained above are dissolved in 400 cc of ethanol, and hydrogenation is effected at 1 atmosphere of hydrogen pressure and 25° with the addition of 0.3 g of a platinic oxide catalyst. After the take up of the calculated amount of hydrogen, filtration is effected and the solvent is concentrated. The resulting β-isobutyl-dihydrocinnamic methyl ester is distilled at 91°–100°/0.02 mm of Hg.

b. 4-carboxymethyl-β-isobutyl-dihydrocinnamic acid, having a M.P. of 143°–147°, is produced from the product obtained in (c) above in a manner analogous to that described in Example 1, (b) to (d).

The compounds of formula Ia indicated in the following Table 1 are also obtained in a manner analogous to Examples 1-3, by cyclization of the corresponding compounds of formula II:

dronaphthalene-2-acetic acid is recrystallized from hexane and has a M.P. of 64°–66°.

Table 1

| Ex. Nr. | $R_1$ | $R_2$ | $R_5^I$ | $R_7^I$ | $R_6^I$ | $A^I$ | M.P. |
|---|---|---|---|---|---|---|---|
| 3A | H | H | H | 6—$CH_3$ | H | —$CH_2$— | 118–120° |
| 3B | H | H | H | 6—CH(CH$_3$)$_2$ | H | —$CH_2$— | 99–101° |
| 3C | H | H | H | 5—CH—$CH_2$—$CH_3$ | H | —$(CH_2)_0$— | 73–75° |
| 3D | H | H | H | 6—$CH_2$—$CH_2$—$CH_3$ | H | —$CH_2$— | 94–96° |
| 3E° | H | H | H | H | \_(CH$_2$)$_3$_/ | | CHA* 176–179° |
| 3F°° | H | H | H | H | \_(CH$_2$)$_4$_/ | | 151–153° |
| 3G | $CH_3$ | H | H | 6—$CH_3$ | H | —$CH_2$— | CHA* 196–199° |
| 3H | $CH_3$ | H | H | 6—$CH_2$—$CH_3$ | H | —$CH_2$— | 128–131° |
| 3J° | $CH_3$ | H | H | H | \_(CH$_2$)$_3$_/ | | CHA* 167–170° (Z)+ |
| 3K | H | H | H | 6—$CH_2CH_3$ | H | —$CH_2$— | 134–136° |
| 3L$^\Delta$ | H | H | H | 7—$CH_3$ | H | —$(CH_2)_2$— | CHA* 136–138° $[\alpha]_D$ − 15° |
| 3M$^{\Delta\Delta}$ | H | H | H | 7—$CH_3$ | H | —$(CH_2)_2$— | CHA* 134–136° $[\alpha]_D$ + 14° |
| 3N | H | H | H | ($\dot{C}H_2$)$_5$ | H | —$(CH_2)_0$— | CHA* 186–190° (Z)+ |

° cis form
°° trans form
*CHA = Cyclohexylammonium salt
+Z = with decomposition
$^\Delta$ (−)-(7R) form
$^{\Delta\Delta}$ (+)-(7S) form

EXAMPLE 4

6-ethyl-5,6,7,8-tetrahydronaphthalene-2-acetic acid 5.4 g of 6-ethyl-5,6,7,8-tetrahydro-8-oxo-naphthalene-2-acetic acid are dissolved in 150 cc of acetic acid and hydrogenation is effected at 4 atmospheres of hydrogen pressure and 45° with the addition of 1 g of palladium/charcoal (10%) and 2 cc of 70% aqueous perchloric acid. After the take up of the calculated amount of hydrogen, filtration is effected, 2 g of sodium acetate are added and the solution is concentrated. The residue is divided between ether and water, the ether extract is dried over sodium sulphate and concentrated by evaporation. The resulting 6-ethyl-5,6,7,8-tetrahy- The compounds of formula Ib indicated in the following Table 2 are also obtained in a manner analogous to that described in Example 4, by reduction of the corresponding keto compounds:

Table 2

| Ex. Nr. | $R_1$ | $R_2$ | $R_3^I$ | $R_4^I$ | $R_5^{II}$ | $R_7^{II}$ | $R_6^{II}$ | $A^{II}$ | M.P. |
|---|---|---|---|---|---|---|---|---|---|
| 4 A | H | H | H | H | H | 6-$CH_3$ | H | —$CH_2$— | 90–92° |
| 4 B | H | H | H | H | H | 6-CH(CH$_3$)$_2$ | H | —$CH_2$— | DPA** 126–129° |
| 4 C | H | H | H | H | H | 7-$CH_3$ | H | —$(CH_2)_2$— | 109–111° |
| 4 E | H | H | H | H | H | 6-$CH_2$—$CH_2$—$CH_3$ | H | —$CH_2$— | 78–80° |
| 4 F° | H | H | H | H | H | H | \_(CH$_2$)$_3$_/ | | CHA* 166–169° |
| 4 G | $CH_3$ | H | H | H | H | 6-$CH_3$ | H | —$CH_2$— | 93–95° |
| 4 H | $CH_3$ | H | H | H | H | 6-$CH_2$—$CH_3$ | H | —$CH_2$— | 84–87° |
| 4 J | $CH_3$ | H | H | H | H | 7-$CH_3$ | H | —$(CH_2)_2$— | CHA* 166–169° |
| 4 K | $CH_3$ | H | H | H | H | 7-$CH_2$—$CH_3$ | H | —$(CH_2)_2$— | CHA* 143–146° |
| 4 L | $CH_3$ | H | H | H | H | H | H | —$(CH_2)_2$— | CHA* 187–190° |
| 4 M $^\Delta$ | H | H | H | H | H | 7-$CH_3$ | H | —$(CH_2)_2$— | 139–142°, $[\alpha]_D$ = −20° |
| 4 N $^{\Delta\Delta}$ | H | H | H | H | H | 7-$CH_3$ | H | —$(CH_2)_2$— | 141–143°, $[\alpha]_D$ = +23° |
| 4 O° | $CH_3$ | H | H | H | H | H | \_(CH$_2$)$_3$_/ | | CHA* 192–195° |
| 4 P | $CH_3$ | H | H | H | H | 6-$CH_2$—$CH_2$—$CH_3$ | H | —$CH_2$— | DPA** 136–137° |

°cis form
*CHA = Cyclohexylammonium salt
**DPA = (1,3-Dihydroxy-2-hydroxymethyl-2-propyl)ammonium salt
$^\Delta$(−)-(7R) form
$^{\Delta\Delta}$(+)-(7S) form

EXAMPLE 5

6,7-dihydro-7-methyl-5H-benzocycloheptene-2-acetic acid 5.9 g of 6,7,8,9-tetrahydro-9-hydroxy-7-methyl-5H-benzocycloheptene-2-acetic acid are dissolved in 50 cc of benzene, 1 g of p-toluenesulphonic acid is added, and the solution is boiled at reflux for 3 hours. The solution is diluted with water, extracted with benzene, the benzene extract is washed with water, dried over sodium sulphate and concentrated by evaporation. The crude 6,7-dihydro-7-methyl-5H-benzocycloheptene-2-acetic acid is purified by chromatography on silica gel. The title compound has a M.P. of 80°–82° (from hexane).

The starting material may be obtained as follows:

a. 6,7,8,9-tetrahydro-7-methyl-9-oxo-5H-benzocycloheptene-2-acetic acid (6.3 g) is dissolved in 90 cc of methanol, and 4.1 g of sodium borohydride are added in small portions within 10 minutes while stirring at room temperature. The solution is stirred for a further 30 minutes, is diluted with water, acidified with 1 N hydrochloric acid, and the crude 6,7,8,9-tetrahydro-9-hydroxy-7-methyl-5H-benzocycloheptene-2-acetic acid is filtered off. The crude product has a M.P. of 161°–163°.

The following compounds are also obtained:

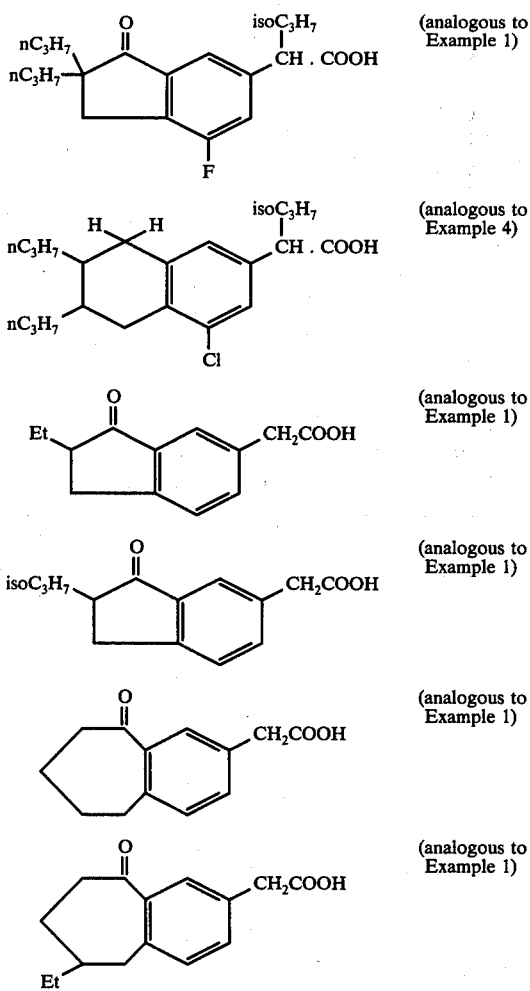

The compounds of formula I are useful because they possess pharmacological activity in animals. In particular the compounds of formula I are useful as analgesic agents for the treatment of pain as indicated in standard tests, e.g. in the phenyl-p-benzoquinone syndrome test in mice on p.o. administration of from 1 to 60 mg/kg animal body weight of the compounds, in the Randall-Selitto test in rats on s.c. and i.p. administration of from 5 to 60 mg/kg animal body weight of the compounds, and in the shock titration test in the rhesus monkey on i.p., p.o. and s.c. administration of from 30 to 60 mg/kg animal body weight of the compounds.

For this use the dosage will, of course, vary depending on the compound employed, mode of administration and treatment desired. However, in general, satisfactory results are obtained when administered at a daily dosage of from 1 mg to about 60 mg per kg animal body weight, conveniently given in divided doses 2 to 4 times a day or in sustained release form. For the larger mammals, the total daily dosage is in the range from about 100 to about 200 mg, and dosage forms suitable for oral administration comprise from about 25 mg to about 100 mg of the compounds admixed with a solid or liquid pharmaceutical carrier or diluent.

The compounds of formula I are furthermore useful because they possess pharmacological activity in animals. In particular, the compounds of formula I are useful as anti-anthritic agents, as indicated in standard tests, for example, by an inhibition of swellings in the Freund adjuvant arthritis latent period test in rats on p.o. administration of from 10 to 100 mg/kg animal body weight of the compounds.

For this use the dosage will, of course, vary depending on the compound employed, mode of administration and treatment desired. However, in general, satisfactory results are obtained with a daily dosage of from about 1 mg to about 100 mg per kg animal body weight, conveniently given in divided doses 2 to 4 times a day or in sustained release form. For the larger mammal, the total daily dosage is in the range of about 100 to about 1000 mg, and dosage forms suitable for oral administration comprise from about 25 mg to about 500 mg of the compounds admixed with a solid or liquid pharmaceutical carrier or diluent.

A preferred daily dosage range is from 300 to 900 mg.

The compounds of formula I are furthermore useful because they possess pharmacological activity in animals. In particular, the compounds of formula I are useful as anti-phlogistic agents for the inhibition of oedemas, as indicated in standard tests, for example, by an inhibition of oedema formation in the carrageen paw oedema test in rats on p.o. administration of from 5 to 100 mg/kg animal body weight of the compounds.

For this use the dosage will, of course, vary depending on the compound employed, mode of administration and treatment desired. However, in general, satisfactory results are obtained with a daily dosage of from about 1 mg to about 100 mg per kg animal body weight, conveniently given in divided doses 2 to 4 times a day or in sustained release form. For the larger mammal, the total daily dosage is in the range from about 100 to about 1000 mg, and dosage forms suitable for oral administration comprise from about 25 mg to about 500 mg of the compounds admixed with a solid or liquid pharmaceutical carrier or diluent.

A preferred daily dosage for larger animals is from 300 to 900 mg.

The compounds of formula Ib may be administered in pharmaceutically acceptable salt form. Such salt forms exhibit the same order of activity as the free acid forms. Representative salt forms include alkali metal salts such as the sodium or potassium salt, alkaline earth metal salts such as the calcium salt and also include organic salts such as the ammonium salt and amine salts such as the dimethylamine, diethylamine, trimethylamine and benzylamine salts. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastro-intestinal tract and thereby provide sustained action over a long period.

In a group of compounds $R_3$ and $R_4$ are together oxygen, $R_1$ is hydrogen or methyl, $R_2$ is hydrogen, $R_5$ and $R_7$ are hydrogen, $R_6$ is methyl, ethyl, n-propyl, isopropyl or isobutyl, and $n$ is 0, 1 or 2.

In another group of compounds $R_3$ and $R_4$ are both hydrogen, $R_1$ is hydrogen or methyl, $R_2$ is hydrogen, $R_5$ and $R_7$ are hydrogen, $R_6$ is methyl, ethyl, n-propyl, iso-propyl or iso-butyl and $n$ is 1 or 2.

In another group of compounds $R_3$ and $R_4$ are together oxygen or both are hydrogen, $R_2$ is hydrogen, $R_5$ and $R_7$ are hydrogen, and $R_6$ and A form a 1,2-cyclopentylene ring.

In a group of compounds $R_5$ and $R_7$ are both hydrogen and $R_6$ is lower alkyl. In a sub-group $R_3$ and $R_4$ are together hydrogen, preferably with $n = 1$.

In a further sub-group $R_3$ and $R_4$ are both hydrogen, preferably with $n = 1$.

In a preferred class $R_1$ is alkyl. In another class $R_1$ is methyl or hydrogen.

In another sub-group $R_6$ and A together with the carbon atom to which they are bound form a cyclopentylene ring or when $R_3$ and $R_4$ are oxygen a cyclohexylene ring.

In a group of compounds $n = 0$, $R_1$ is hydrogen or alkyl of 1 or 2 carbon atoms; $R_2$ is hydrogen; $R_3$ and $R_4$ together are oxygen; $R_5$ is hydrogen or alkyl of 1 to 4 carbon atoms, $R_6$ is hydrogen or alkyl of 1 to 4 carbon atoms; $R_7$ is attached to any carbon atom of ring B except those marked * in the formula and is hydrogen or, provided that $R_6$ is hydrogen, $R_7$ may alternatively be alkyl or 1 to 4 carbon atoms; or $R_5$ and $R_7$ are attached to the same carbon atom and form an alkylene chain of 3 to 6 carbon atoms.

In a group of compounds $n = 0$, $R_1$ is hydrogen or alkyl of 1 to 2 carbon atoms; $R_2$ is halogen of atomic number from 9 to 35; $R_3$ and $R_4$ together are oxygen; $R_5$ is hydrogen or alkyl of 1 to 4 carbon atoms, $R_6$ is hydrogen or alkyl of 1 to 4 carbon atoms; $R_7$ is attached to any carbon atom of ring B except those marked * in the formula and is hydrogen or, provided that $R_6$ is hydrogen, $R_7$ may alternatively be alkyl of 1 to 4 carbon atoms, or $R_5$ and $R_7$ are attached to the same carbon atom and form an alkylene chain of 3 to 6 carbon atoms.

In a group of compounds $n$ is 1, $R_1$ is hydrogen or alkyl of 1 to 2 carbon atoms; $R_2$ is hydrogen; each of $R_3$ and $R_4$ is hydrogen and at least one of $R_5$, $R_6$ and $R_7$ as hereinbefore defined is alkyl of 1 to 4 carbon atoms.

In a group of compounds $n$ is 1, $R_1$ is hydrogen or alkyl of 1 or 2 carbon atoms; $R_2$ is halogen of atomic number from 9 to 35, each of $R_3$ and $R_4$ is hydrogen and at least one of $R_5$, $R_6$ and $R_7$ as hereinbefore defined is alkyl of 1 to 4 carbon atoms.

In a group of compounds $n = 1$, $R_1$ is hydrogen or alkyl of 1 or 2 carbon atoms, $R_2$ is hydrogen, $R_3$ and $R_4$ together are oxygen and at least one of $R_5$, $R_6$ and $R_7$ as hereinbefore defined is alkyl of 1 to 4 carbon atoms.

In a group of compounds $n = 1$, $R_1$ is hydrogen or alkyl of 1 to 2 carbon atoms, $R_2$ is halogen of atomic number from 9 to 35, $R_3$ and $R_4$ together are oxygen and at least one of $R_5$, $R_6$ and $R_7$ as hereinbefore defined is alkyl of 1 to 4 carbon atoms.

In a group of compounds $n = 2$, $R_1$ is hydrogen or alkyl of 1 or 2 carbon atoms, $R_2$ is hydrogen, $R_3$ and $R_4$ together are oxygen, $R_5$ is hydrogen or alkyl of 1 to 4 carbon atoms, $R_6$ is hydrogen or alkyl of 1 to 4 carbon atoms; $R_7$ is attached to any carbon atom of ring B except those marked * in the formula and is hydrogen or, provided that $R_6$ is hydrogen $R_7$ may alternatively be alkyl of 1 to 4 carbon atoms; or $R_5$ and $R_7$ are attached to the same carbon atom and form an alkylene chain of 3 to 6 carbon atoms.

In a group of compounds $n = 2$, $R_1$ is hydrogen or alkyl of 1 or 2 carbon atoms, $R_2$ is hydrogen, $R_3$ is hydrogen and $R_4$ and $R_5$ together form a bond, $R_6$ is hydrogen or alkyl of 1 to 4 carbon atoms, $R_7$ is attached to any carbon atom of ring B except those marked * in the formula and is hydrogen or, provided that $R_6$ is hydrogen $R_7$ may alternatively be alkyl of 1 to 4 carbon atoms.

In a group of compounds $n = 2$, each of $R_2$, $R_3$ and $R_4$ is hydrogen and at least one of the substituents $R_1$, $R_5$, $R_6$ and $R_7$ is alkyl of 1 to 4 carbon atoms.

In a group of compounds $n = 2$, $R_1$ is hydrogen or alkyl of 1 or 2 carbon atoms, each of $R_2$, $R_3$, $R_4$, $R_5$ and $R_7$ is hydrogen and R and A are together with the carbon atoms to which they bound a 1,2-cycloalkylene group of formula:

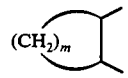

wherein $m$ is 3.

In a group of compounds $n = 2$, $R_1$ is hydrogen or alkyl of 1 or 2 carbon atoms, each of $R_2$, $R_5$ and $R_7$ is hydrogen, $R_3$ and $R_4$ together are oxygen, $R_6$ and A are together with the carbon atom to which they are bound a 1,2-cycloalkylene group of formula

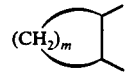

wherein $m$ is 3 or 4.

In a group of compounds $n = 0$, $R_1$ is hydrogen or methyl, $R_2$ is hydrogen, $R_3$ and $R_4$ together are oxygen. $R_5$ is hydrogen or alkyl of 1 to 4 carbon atoms, $R_6$ is hydrogen or alkyl of 1 to 4 carbon atoms, and $R_7$ is attached to the same carbon atom as $R_5$ and is hydrogen or provided that $R_6$ is hydrogen, $R_7$ may alternatively be alkyl of 1 to 4 carbon atoms.

I claim:
1. A compound of the formula

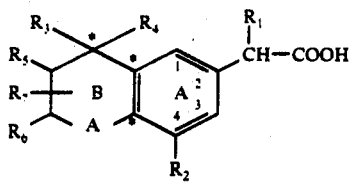

where
- R₁ is hydrogen or alkyl of 1 or 2 carbon atoms,
- R₂ is hydrogen,
- R₃ and R₄ together are oxygen,
- R₅ is hydrogen or alkyl of 1 to 4 carbon atoms,
- R₆ is hydrogen or alkyl of 1 to 4 carbon atoms;
- R₇ is attached to any carbon atom of ring B except those marked * in the formula and is hydrogen or, provided that R₆ is hydrogen, R₇ may alternatively be alkyl of 1 to 4 carbon atoms; or
- R₅ and R₇ are attached to the same carbon atoms and form an alkylene chain of 3 to 6 carbon atoms, and
- A is —(CH₂)₂—.

2. A compound of the formula

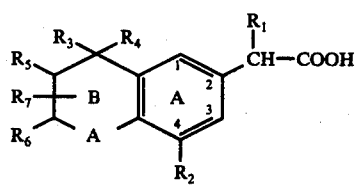

where
- R₁ is as defined in claim 1, and
- each of R₂, R₃, R₄, R₅ and R₇ is hydrogen, and
- R₆ and A together with the carbon atoms to which they are bound are a 1,2-cycloalkylene group of the formula

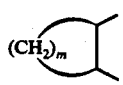

where
- m is 3 and
- A is —(CH₂)₂—.

3. A compound of the formula

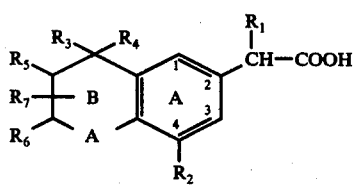

where
- R₁ is as defined in claim 1,
- each of R₂, R₅ and R₇ is hydrogen,
- R₃ and R₄ together are oxygen,
- R₆ and A together with the carbon atoms to which they are bound are a 1,2-cycloalkylene group of the formula

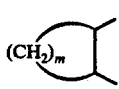

where
- m is 3 or 4, and
- A is —(CH₂)₂—.

4. A compound of claim 1 in 7R form.
5. A compound of claim 1 in 7S form.
6. A compound of the formula

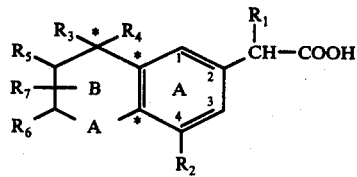

where
- R₁ is hydrogen or alkyl of 1 or 2 carbon atoms,
- R₂ is hydrogen,
- R₃ is hydrogen,
- R₄ and R₅ together from a bond,
- R₆ is hydrogen or alkyl of 1 to 4 carbon atoms,
- R₇ is attached to any carbon atom of ring B except those marked * in the formula and is hydrogen or, provided that R₆ is hydrogen, R₇ may alternatively be alkyl of 1 to 4 carbon atoms, and
- A is —(CH₂)₂—.

7. A compound of claim 6 in 7R form.
8. A compound of claim 6 in 7S form.
9. A compound of the formula

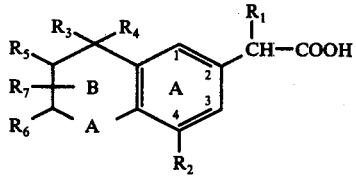

where each of R₂, R₃ and R₄ is hydrogen and at least one of the substituents R₁, R₅, R₆ and R₇ is alkyl of 1 to 4 carbon atoms, and A is —(CH₂)₂—.

10. A compound of claim 9 in 7R form.
11. A compound of claim 9 in 7S form.
12. The compound of claim 9 which is 6,7,8,9-tetrahydro-7-methyl-9-oxo-5H-bezocycloheptene-2-acetic acid.
13. A method of treating inflammations in animals which comprises administering to an animal in need of such treatment a therapeutically effective amount of a compound of claim 1.
14. A method of treating inflammations in animals which comprises administering to an animal in need of such treatment a therapeutically effective amount of a compound of claim 6.
15. A method of treating inflammations in animals which comprises administering to an animal in need of such treatment a therapeutically effective amount of a compound of claim 9.
16. A pharmaceutical composition comprising an effective amount of a compound of claim 1 in association with a pharmaceutical carrier or diluent.
17. A pharmaceutical composition comprising an effective amount of a compound of claim 6 in association with a pharmaceutical carrier or diluent.
18. A pharmaceutical composition comprising an effective amount of a compound of claim 9 in association with the pharmaceutical carrier or diluent.

* * * * *